(12) United States Patent
Dubois

(10) Patent No.: US 7,282,604 B2
(45) Date of Patent: Oct. 16, 2007

(54) METHOD FOR THE PRODUCTION OF ACRYLIC ACID FROM PROPANE, IN THE ABSENCE OF MOLECULAR OXYGEN

(75) Inventor: Jean-Luc Dubois, Millery (FR)

(73) Assignee: Arkema, Puteaux (FR)

( * ) Notice: Subject to any disclaimer, the term of this patent is extended or adjusted under 35 U.S.C. 154(b) by 199 days.

(21) Appl. No.: 10/527,059

(22) PCT Filed: Aug. 29, 2003

(86) PCT No.: PCT/FR03/02608

§ 371 (c)(1),
(2), (4) Date: Mar. 9, 2005

(87) PCT Pub. No.: WO2004/024664

PCT Pub. Date: Mar. 25, 2004

(65) Prior Publication Data

US 2006/0004225 A1    Jan. 5, 2006

(30) Foreign Application Priority Data

Sep. 10, 2002  (FR) .................................. 02 11196

(51) Int. Cl.
C07C 51/16   (2006.01)
(52) U.S. Cl. ................................................. 562/549
(58) Field of Classification Search .................... None
See application file for complete search history.

(56) References Cited

U.S. PATENT DOCUMENTS 4,606,810 A    8/1986  Krambeck et al.
4,830,728 A    5/1989  Herbst et al.
4,874,503 A   10/1989  Herbst et al.
4,966,681 A   10/1990  Herbst et al.
5,198,590 A    3/1993  Sofranko et al.
6,287,522 B1   9/2001  Lomas
6,310,240 B1  10/2001  Contractor et al.
6,833,474 B2 * 12/2004  Dubois ....................... 562/549

FOREIGN PATENT DOCUMENTS

| EP | 0 034 442 A2 | | 8/1981 |
|---|---|---|---|
| EP | 1 238 960 A1 | | 9/2002 |
| JP | 03-170445 | * | 7/1991 |
| JP | 2002-88012 | | 3/2002 |
| WO | WO 02/0051542 A1 | | 7/2002 |
| WO | WO 03/004886 A2 | | 6/2003 |

OTHER PUBLICATIONS

International Search Report PCT/ISA/210.

* cited by examiner

*Primary Examiner*—Paul A. Zuclker
(74) *Attorney, Agent, or Firm*—Buchanan Ingersoll & Rooney PC

(57) ABSTRACT

The invention concerns a method for producing acrylic acid from propane, in the absence of molecular oxygen which consists in: a) introducing a gas mixture free of molecular oxygen and comprising propane, water vapor, and, optionally, an inert gas, into a first reactor with fluidized catalytic bed, b) at the first reactor output, separating the gases from the catalyst, c) recycling the catalyst into a regenerator, d) introducing the gases into a second reactor with fluidized catalytic bed, e) at the second reactor output, separating the gases from the catalyst and recovering acrylic acid contained in the separated gases, f) recycling the catalyst into the regenerator, and g) reintroducing the regenerated catalyst from the regenerator into the first and second reactors.

24 Claims, 1 Drawing Sheet

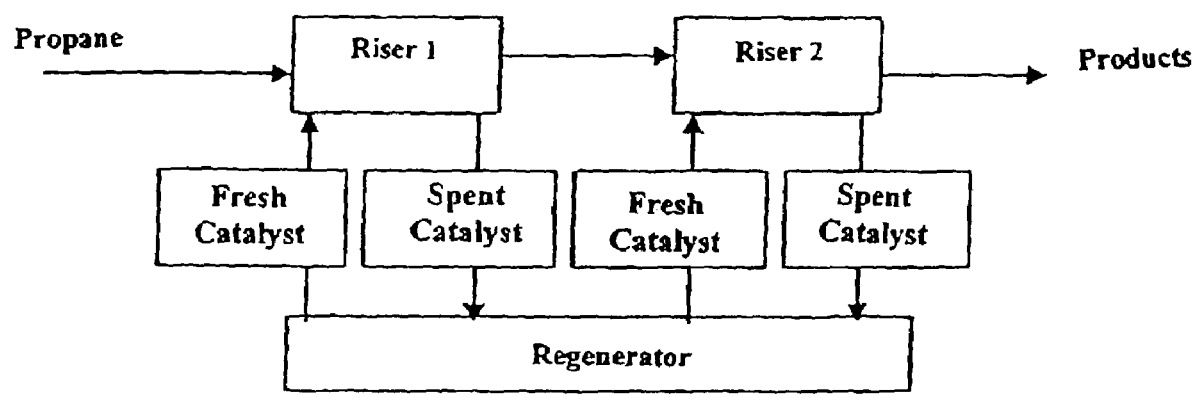
Single figure

METHOD FOR THE PRODUCTION OF ACRYLIC ACID FROM PROPANE, IN THE ABSENCE OF MOLECULAR OXYGEN

The present invention relates to the production of acrylic acid from propane in the absence of molecular oxygen.

It is known from European patent application No. EP-A-608838 how to prepare an unsaturated carboxylic acid from an alkane according to a catalytic oxidation reaction in vapor phase in the presence of a catalyst containing a mixed metal oxide comprising as essential components, Mo, V, Te, O, as well as at least one element chosen from the group constituted by niobium, tantalum, tungsten, titanium, aluminum, zirconium, chromium, manganese, iron, ruthenium, cobalt, rhodium, nickel, palladium, platinum, antimony, bismuth, boron, indium and cerium, these elements being present in very precise proportions. The uses of such a catalyst devoid of silicon described in the examples of this document lead to good acrylic acid selectivities but they are implemented in the presence of air.

Moreover, patents such as the American U.S. Pat. Nos. 4,606,810, 4,966,681, 4,874,503, 4,830,728, 5,198,590 and 6,287,522 use two or more reactors, called "Risers", however these patents only relate to applications in the refinery of petroleum cuts.

The aim of the invention is therefore to provide a method for the production of acrylic acid from propane and in the absence of molecular oxygen, which allows a high conversion of the propane to be obtained while having a high selectivity.

The Applicant has discovered that this aim can be achieved by passing a gas mixture of propane and water vapor, and if appropriate, of an inert gas, over a particular catalyst, which acts as a redox system and provides the oxygen necessary for the reaction and by using an apparatus having two reaction zones.

The advantages of this novel method are the following:
the limitation of the overoxidation of the products formed which takes place in the presence of molecular oxygen; according to the present invention, due the fact of operating in the absence of molecular oxygen, the formation of $CO_x$ (carbon monoxide and carbon dioxide), degradation products, is reduced, which allows the acrylic acid selectivity to be increased;
the acrylic acid selectivity is maintained at a good level;
the conversion is increased without loss of selectivity;
the catalyst does not undergo a low reduction and therefore a progressive loss of its activity; it can easily be regenerated by heating in the presence of oxygen or of a gas containing oxygen after a certain period of use; after regeneration, the catalyst regains its initial activity and can be used in another reaction cycle;
moreover, the separation of the stages of reduction of the catalyst and of regeneration of the latter allows the partial pressure of propane to be increased, such a partial supply pressure of propane no longer being limited by the existence of an explosive zone created by the propane+oxygen mixture.

The subject of the present invention is therefore a process for manufacturing acrylic acid from propane, in which:
a) a gas mixture free from molecular oxygen and comprising propane, water vapor, as well as, if appropriate, an inert gas, is introduced into a first reactor with a moving catalyst bed,
b) at the outlet of the first reactor, the gases are separated from the catalyst,
c) the catalyst is returned into a regenerator,
d) the gases are introduced into a second reactor with a moving catalyst bed,
e) at the outlet of the second reactor, the gases are separated from the catalyst and the acrylic acid contained in the separated gases is recovered,
f) the catalyst is returned into the regenerator,
g) the regenerated catalyst from the regenerator is reintroduced into the first and second reactors, and in which the catalyst comprises molybdenum, vanadium, tellurium or antimony, oxygen and at least one other element X chosen from niobium, tantalum, tungsten, titanium, aluminum, zirconium, chromium, manganese, iron, ruthenium, cobalt, rhodium, nickel, palladium, platinum, antimony, bismuth, boron, indium and cerium.

This method allows an acrylic acid selectivity to be obtained of close to 60% and a high conversion of the propane.

BRIEF DESCRIPTION OF THE SEVERAL VIEWS OF THE DRAWING

FIG. 1 is a simplified schematic representation of process steps according to an embodiment of the present invention.

Other characteristics and advantages of the invention will now be described in detail in the following description which is given with reference to the single attached figure, which diagrammatically represents an apparatus which is suitable for the implementation of the method according to the invention.

DETAILED DESCRIPTION OF THE INVENTION

The operation of the method according to the invention can be explained with reference to the attached figure.

The gas mixture comprising propane, water vapor, as well as, if appropriate, an inert gas, is introduced into a first reactor (Riser 1) containing the moving catalyst bed.

Then, at the outlet of the first reactor, the effluents are separated into gases and the moving bed catalyst.

The catalyst is sent into a regenerator.

The gases are introduced into a second reactor (Riser 2) also containing a moving catalyst bed.

At the outlet of the second reactor, the effluents are separated into gases and the catalyst.

The catalyst is sent into a regenerator.

The gases are treated in a known way, generally by absorption and purification, with a view to recovering the acrylic acid produced.

The regenerated catalyst is reintroduced into the first reactor as well as into the second reactor.

The method thus operates continuously, the circulation of the catalyst between the reactors and the regenerator is carried out in a regular and generally continuous way.

Of course, the single regenerator can be replaced by two or more regenerators.

Moreover, it is possible to add, after the second reactor, other reactors which also have a catalyst circulating between each of these reactors and the regenerator or other regenerators.

Preferably, the first and second reactors are vertical and the catalyst is transported upwards by the gas flow.

As regards the conversion of propane to acrylic acid using the catalyst, it is carried out according to the following redox reaction (1):

$$SOLID_{oxidized} + PROPANE \rightarrow SOLID_{reduced} + ACRYLIC\ ACID \quad (1)$$

Generally, this redox reaction (1) is carried out at a temperature of 200 to 500° C., preferably 250 to 450° C., even more preferably, 350 to 400° C.

The pressure in the reactors is generally from $1.01 \times 10^4$ to $1.01 \times 10^6$ Pa (0.1 to 10 atmospheres), preferably from $5.05 \times 10^4$ to $5.05 \times 10^5$ Pa (0.5-5 atmospheres).

The residence time in each reactor is generally from 0.01 to 90 seconds, preferably, from 0.1 to 30 seconds.

The propane/water vapor volume ratio in the gas phase is not critical and can vary within wide limits.

Similarly, the proportion of inert gas, which can be helium, krypton, a mixture of these two gases, or nitrogen, carbon dioxide, etc., is also not critical and can also vary within wide limits.

As regards the order of magnitude of the proportions of the initial mixture, the following ratio can be mentioned (in volumes):

propane/inert (He—Kr)/H$_2$O (vapor): 10-30/40-50/40-50

As regards the catalyst, the proportions of its constituent elements can meet the following conditions:

$$0.25 < r_{Mo} < 0.98$$

$$0.003 < r_V < 0.5$$

$$0.003 < r_{Te\ or\ rSb} < 0.5$$

$$0.003 < r_X < 0.5$$

in which $r_{Mo}$, $r_V$, $r_{Te}$ or $r_{Sb}$ and $r_X$ represent the mole fractions, respectively, of Mo, V, Te and X, in relation to the sum of the number of moles of all the elements of the catalyst, with the exception of oxygen. Such a catalyst can be prepared according to the teaching of the above-mentioned European patent application No. 608 838. Reference can be made in particular, to the catalyst of formula $Mo_1V_{0.3}Te_{0.23}Nb_{0.12}O_n$ the preparation of which is described in Example 1 of this patent application.

According to a preferred embodiment of the invention, the catalyst corresponds to formula (I) or to formula (Ia) below:

$$Mo_1V_aTe_bNb_cSi_dO_x \quad (I)$$

$$Mo_1V_aSb_bNb_cSi_dO_x \quad (Ia)$$

in which:
a is comprised between 0.006 and 1, inclusive;
b is comprised between 0.006 and 1, inclusive;
c is comprised between 0.006 and 1, inclusive;
d is comprised between 0 and 3.5, inclusive; and
x is the quantity of oxygen bound to the other elements and depends on their oxidation state.

Advantageously:
a is comprised between 0.09 and 0.8, inclusive;
b is comprised between 0.04 and 0.6, inclusive;
c is comprised between 0.01 and 0.4, inclusive; and
d is comprised between 0.4 and 1.6, inclusive.

The oxides of the different metals included in the composition of the catalyst of formula (I) or (Ia) can be used as raw materials in the preparation of this catalyst, but the raw materials are not limited to the oxides; as other raw materials, there may be mentioned:

in the case of molybdenum, ammonium molybdate, ammonium paramolybdate, ammonium heptamolybdate, molybdic acid, molybdenum halides or oxyhalides such as MoCl$_5$, organometallic compounds of molybdenum such as molybdenum alkoxides such as Mo(OC$_2$H$_5$)$_5$, acetylacetone molybdenyl;

in the case of vanadium, ammonium metavanadate, vanadium halides or oxyhalides such as VCl$_4$, VCl$_5$ or VOCl$_3$, the organometallic compounds of vanadium such as vanadium alkoxides such as VO(OC$_2$H$_5$)$_3$;

in the case of tellurium, tellurium, telluric acid and TeO$_2$;

in the case of niobium, niobic acid, Nb$_2$(C$_2$O$_4$)$_5$, niobium tartrate, niobium hydrogen oxalate, oxotrioxalatoammonium niobate {(NH$_4$)$_3$[NbO(C$_2$O$_4$)$_3$].1.5H$_2$O}, niobium and ammonium oxalate, niobium oxalate and tartrate, nobium halides or oxyhalides such as NbCl$_3$, NbCl$_5$ and organometallic compounds of niobium such as niobium alkoxides such as Nb(OC$_2$H$_5$)$_5$, Nb(O-n-Bu)$_5$;

and, generally, all the compounds which are able to form an oxide by calcination, namely, the metallic salts of organic acids, the metallic salts of mineral acids, the metal complex compounds, etc.

The source of silicon is generally constituted by colloidal silica and/or polysilicic acid.

According to particular embodiments, the catalyst of formula (I) can be prepared by mixing aqueous solutions of niobic acid, ammonium heptamolybdate, ammonium metavanadate, telluric acid under stirring, by the addition preferably of colloidal silica, then by precalcinating under air at approximately 300° C. and by calcinating under nitrogen at approximately 600° C.

Preferably, in the catalyst of formula (I) or(Ia):
a is comprised between 0.09 and 0.8, inclusive;
b is comprised between 0.04 and 0.6, inclusive;
c is comprised between 0.01 and 0.4, inclusive; and
d is comprised between 0.4 and 1.6, inclusive.

During the redox reaction (1), the catalyst undergoes reduction and a progressive loss of its activity. This is why, once the catalyst has at least partially changed to the reduced state, its regeneration is carried out according to reaction (2):

$$SOLID_{reduced} + O_2 \rightarrow SOLID_{oxidized} \quad (2)$$

by heating in the presence of oxygen or a gas containing oxygen at a temperature of 250 to 500° C., for a time necessary for the reoxidation of the catalyst.

Generally the method is carried out until the reduction ratio of the catalyst is comprised between 0.1 and 10 g of oxygen per kg of catalyst.

This reduction ratio can be monitored during the reaction through the quantity of products obtained. Then the equivalent quantity of oxygen is calculated. It can also be monitored through the exothermicity of the reaction.

After regeneration, which can be carried out under temperature and pressure conditions which are identical to, or different from those of the redox reaction, the catalyst regains an initial activity and can be reintroduced into the reactors.

A method of operating with only one passage or with recycling of the products leaving the second reactor can be used.

According to a preferred embodiment of the invention, after treatment of the gas originating from the second reactor, the propylene produced as by-product and/or the propane which has not reacted are recycled (or returned) to the inlet of the reactor, i.e. they are reintroduced at the inlet of the first reactor, in a mixture or in parallel with the initial mixture of propane, water vapor and if appropriate of inert gas or gases.

According to an advantageous embodiment of the invention, the gas mixture also passes over a cocatalyst.

This has the advantage of reducing the production of propionic acid, which is generally a by-product of the conversion reaction and which poses problems in certain applications of acrylic acid when it is present in too great a quantity.

Thus, the propionic acid/acrylic acid ratio is greatly reduced at the outlet of the reactor.

Moreover, the formation of acetone, which is also a by-product of the production of acrylic acid from propane, is reduced.

To this end, at least one of the reactors comprises a cocatalyst with the following formula (II):

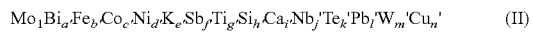

$$Mo_1Bi_{a'}Fe_{b'}Co_{c'}Ni_{d'}K_{e'}Sb_{f'}Ti_{g'}Si_{h'}Ca_{i'}Nb_{j'}Te_{k'}Pb_{l'}W_{m'}Cu_{n'} \quad (II)$$

in which:
a' is comprised between 0.006 and 1, inclusive;
b' is comprised between 0 and 3.5, inclusive;
c' is comprised between 0 and 3.5, inclusive;
d' is comprised between 0 and 3.5, inclusive;
e' is comprised between 0 and 1, inclusive;
f' is comprised between 0 and 1, inclusive;
g' is comprised between 0 and 1, inclusive;
h' is comprised between 0 and 3.5, inclusive;
i' is comprised between 0 and 1, inclusive;
j' is comprised between 0 and 1, inclusive;
k' is comprised between 0 and 1, inclusive;
l' is comprised between 0 and 1, inclusive;
m' is comprised between 0 and 1, inclusive; and
n' is comprised between 0 and 1, inclusive.

Such a cocatalyst can be prepared in the same way as the catalyst of formula (I).

The oxides of the different metals included in the composition of the cocatalyst of formula (II) can be used as raw materials in the preparation of this cocatalyst, but the raw materials are not limited to the oxides; as other raw materials, the corresponding nitrates can be mentioned in the case of nickel, cobalt, bismuth, iron or potassium.

Generally, the cocatalyst is present in the form of a moving bed and it is regenerated and circulates in the same way as the catalyst.

Preferably, in the cocatalyst of formula (II):
a' is comprised between 0.01 and 0.4, inclusive;
b' is comprised between 0.2 and 1.6, inclusive;
c' is comprised between 0.3 and 1.6, inclusive;
d' is comprised between 0.1 and 0.6, inclusive;
e' is comprised between 0.006 and 0.01, inclusive.
f' is comprised between 0 and 0.4, inclusive;
g' is comprised between 0 and 0.4, inclusive;
h' is comprised between 0.01 and 1.6, inclusive;
i' is comprised between 0 and 0.4, inclusive;
j' is comprised between 0 and 0.4, inclusive;
k' is comprised between 0 and 0.4, inclusive;
l' is comprised between 0 and 0.4, inclusive;
m' is comprised between 0 and 0.4, inclusive; and
n' is comprised between 0 and 0.4, inclusive.

The weight ratio of the catalyst to the cocatalyst is generally greater than 0.5 and preferably at least 1.

Advantageously, the cocatalyst is present in the two reactors.

The catalyst and the cocatalyst are present in the form of solid catalytic compositions.

They can each be in the form of pellets, generally of 20 to 300 μm in diameter, the catalyst and cocatalyst pellets generally being mixed before implementation of the method according to the invention.

The catalyst and the cocatalyst can also be present in the form of a solid catalytic composition composed of pellets each of which comprises both the catalyst and the cocatalyst.

EXAMPLES

The following examples illustrate the present invention without limiting its scope.

In the formulae given in Example 1, x is the quantity of oxygen bound to the other elements and depends on their oxidation states.

The conversions, selectivities and yields are defined as follows:

$$\text{Conversion}(\%) = \frac{\text{Number of moles of propane having reacted}}{\text{Number of moles of propane introduced}} \times 100$$

$$\frac{\text{Selectivity}(\%)}{\text{for acrylic acid}} = \frac{\text{Number of moles of acrylic acid formed}}{\text{Number of moles of propane having reacted}} \times 100$$

$$\frac{\text{Yield}(\%)}{\text{of acrylic acid}} = \frac{\text{Number of moles of acrylic acid formed}}{\text{Number of moles of propane introduced}} \times 100$$

The selectivities and yields relating to the other compounds are calculated in a similar way.

The conversion ratio is the weight of catalyst (in kg) required to convert 1 kg of propane.

Example 1

Preparation of the Catalyst of $Mo_1V_{0.33}Nb_{0.11}Te_{0.22}Si_{0.95}O_x$ a) Preparation of a Solution of Niobium 640 g of distilled water then 51.2 g of niobic acid (i.e. 0.304 moles of niobium) are introduced into a 5 l beaker. Then 103.2 g (0.816 moles) of dihydrated oxalic acid is added.

The molar ratio oxalic acid/niobium is therefore 2.69.

The solution obtained previously is heated at 60° C. for 2 hours, being covered so as to avoid evaporation and with stirring. Thus a white suspension is obtained which is left to cool to 30° C. under stirring, which takes approximately 2 hours.

b) Preparation of a Solution of Mo, V and Te 2120 g of distilled water, 488 g of ammonium heptamolybdate (i.e. 2.768 moles of molybdenum), 106.4 g of ammonium metavanadate $NH_4VO_3$ (i.e. 0.912 moles of vanadium) and 139.2 g of telluric acid (supplier: FLUKA) (i.e. 0.608 moles of tellurium) are introduced into a 5 l beaker.

The solution obtained previously is heated at 60° C. for 1 hour and 20 minutes, being covered so as to avoid evaporation and with stirring. In this way a clear red solution is obtained which is left to cool to 30° C. under stirring, which takes approximately 2 hours.

c) Introduction of the Silica 393.6 g of Ludox silica (containing 40% by weight of silica, supplied by Dupont) is introduced under stirring into the previously prepared solution of Mo, V and Te. The latter retains its limpidity and its red colouring.

Then the previously prepared solution of niobium is added. In this way a fluorescent orange gel is obtained after stirring for a few minutes. This solution is then dried by atomization. The atomizer used is a laboratory atomizer (ATSELAB from Sodeva). The atomization takes place in a nitrogen atmosphere (in order to prevent any oxidation and any untimely combustion of the oxalic acid present in the slurry).

The working parameters are globally:
flow rate of nitrogen of the order of 45 $Nm^3/h$;
flow rate of slurry of the order of 500 g/h;
inlet temperature of the gas comprised between 155° C. and 170° C.;
outlet temperature of the gas comprised between 92° C. and 100° C.

Then the product recovered (355.2 g), which has a particle size less than 40 microns, is placed in an oven overnight at 130° C., in a Teflon-covered plate.

In this way 331 g of dry product is obtained.

d) Calcination

The precalcinations and calcinations were carried out under air and nitrogen flow in steel capacitors. These capacitors are directly installed in muffle furnaces and the air is supplied via the flue. An internal thermometer well allows precise monitoring of the temperature. The cover is useful to prevent air returning towards the catalyst.

Firstly, the 331 g of precursor obtained previously are precalcinated for 4 hours at 300° C. under air flow of 47.9 ml/min/g of precursor.

The solid obtained is then calcinated for 2 hours at 600° C. under a nitrogen flow of 12.8 ml/min/g of solid.

In this way the desired catalyst is obtained.

Example 2

Catalyst Tests a) Apparatus

In order to simulate the method according to the invention, simulations were carried out in a laboratory fixed bed reactor, by generating propane pulses and oxygen pulses. Using a loading of the reactor with two superposed catalyst beds, we can thus simulate the behaviour of the catalyst and what it would have experienced in two successive reactors with a rising moving bed called "risers".

i) A Single Reactor (by Way of Comparison):
test called "single RISER"
The following are loaded from the bottom to the top of a vertical reactor with cylindrical shape and made of Pyrex:
a first height of 1 ml of silicon carbide in the form of particles of 0.125 mm in diameter,
a second height of 1 ml of silicon carbide in the form of particles of 0.062 mm in diameter,
a third height of 5 g of catalyst in the form of particles of 0.02 to 1 mm diluted with 5 ml of silicon carbide in the form of particles of 0.062 mm in diameter,
a fourth height of 1 ml of silicon carbide in the form of particles of 0.062 mm in diameter,
a fifth height of 3 ml of silicon carbide in the form of particles of 0.125 mm in diameter,
a sixth height of 1 ml of silicon carbide in the form of particles of 0.062 mm in diameter,
a seventh height of 5 ml of silicon carbide in the form of particles of 0.062 mm in diameter,
an eighth height of 1 ml of silicon carbide in the form of particles of 0.062 mm in diameter,
a ninth height of 2 ml of silicon carbide in the form of particles of 0.125 mm in diameter,
then, a tenth height of silicon carbide in the form of particles of 1.19 mm so as to fill all of the reactor.

ii) Two Reactors (According to the Invention):
test called "double RISER"
The apparatus is the same as previously, except that the seventh height of 5 ml silicon carbide is replaced by 5 g of catalyst diluted with 5 ml of silicon carbide 0.062 mm, the same as the third catalyst height.

Two catalyst beds are therefore loaded, one above the other in the reactor, which allows simulation of the behaviour of an apparatus with 2 reactors such as the one represented in the attached figure.

b) Operating Method

The reactor is then heated to 250° C. and the vaporiser to 200° C. The electric initiation of the water pump is actuated.

Once the reactor and the vaporiser have reached the temperatures given above, the water pump is actuated and the temperature of the reactor is raised to the desired test temperature.

The hot spot of the reactor is then left to stabilize for 30 minutes.

Then, oxygen is introduced in 10 pulses of 23 seconds each in order to sufficiently oxidize the catalyst. The catalyst is considered to be totally oxidized when the temperature of the hot spot has stabilized, i.e. when there is no more exothermal activity due to the reaction (by monitoring the catalyst temperature measured using a thermocouple placed in the catalyst bed, the fluctuations in temperature can be seen as a function of the pulses).

The pressure at the inlet of the reactor was approximately 1.2 to 1.8 bars (absolute) and the pressure drop across the reactor is approximately 0.2 to 0.8 bars (relative).

As regards the production itself of acrylic acid, a redox balance is composed of 60 redox cycles. A redox cycle represents:
13.3 seconds of propane in a continuous flow of helium-krypton/water,
45 seconds of continuous flow of helium-krypton/water,
20 seconds of oxygen in a continuous flow of helium-krypton/water,
45 seconds of continuous flow of helium-krypton/water.

During the balancing, four samples are taken, each representing 15 cycles. 4 samples of gas are also carried out using gas bags, each sample representing 15 cycles. (The gas samples are carried out over a period corresponding to a multiple of the duration of a cycle, in order to be able to know the theoretical quantity of propane injected).

Each small gas-washing bottle (with a 25 ml capacity and filled with 20 ml of water) is equipped with a gas bag, and when the bottle is connected to the outlet of the reactor (as soon as the liquid bubbles), the bag is open and the chronometer is started.

In order to verify the oxidation state of the catalyst, another series of ten 23-second pulses of oxygen is carried out. It shows that the oxidation state of the solid has been maintained during the balancing (no exothermal activity).

The liquid effluents are analyzed on a HP 6890 chromatograph, after having carried out a specific calibration.

The gases are analyzed during the balancing on a Chrompack micro-GC chromatograph.

An assay of the acidity is carried out on each bottle during the balancing, in order to determine the exact number of moles of acid produced and to validate the chromatographic analyses.

c) Results

The final results correspond to the average of the microbalances carried out on the 4 gas-washing bottles and the 4 gas bags.

A balance is composed of 60 cycles with partial pressures of propane and of oxygen corresponding to the following ratios:

for the reaction: Propane/He—Kr/$H_2O$: 10/45/1945
for the regeneration: $O_2$/He—Kr/$H_2O$: 20/45/45

The flow rate of He/Kr is 4.325 Nl/h (Nl=liter of gas at 0° C. and under 760 mm Hg)

The results are brought together in the following table:

further increase the conversion is therefore to remove the spent catalyst and to replace it with fresh catalyst, this occurring, without changing the flow of catalyst. It is therefore the conversion ratio on 1 bed which is used to calculate the dimensions of the unit.

The results are good, the selectivity for acrylic acid (AA) being close to 60% at 360° C. and at 380° C. The conversion of the propane (Pan) with the method according to the invention is clearly greater than that of the method used comparatively, it is practically twice as great at 360° C.

The yields of acrylic acid are greater than 17.5% at all the temperatures tested, while according to the comparative

| | Description of catalyst test | | | | | | |
|---|---|---|---|---|---|---|---|
| | "Single RISER" test (Comparative) 5 g of catalyst diluted in 5 ml of SiC large bulbous vessel | | | | "Double RISER" test (Invention) 2 beds of 5 g of catalyst diluted in 5 ml of SiC large bulbous vessel | | |
| Temperature (° C.) | 380 | 400 | 360 | 380 | 380 | 400 | 360 |
| Selectivities (%) | | | | | | | |
| Acrylic acid | 57.9 | 57.2 | 57.1 | 60.4 | 58.4 | 49.4 | 58.4 |
| Acetic acid | 10.6 | 6.8 | 10.7 | 8.2 | 9.4 | 6.5 | 11.3 |
| Acrolein | 0.20 | 0.08 | 0.17 | 0.10 | 0.06 | 0.08 | 0.00 |
| Acetone | 1.06 | 0.49 | 2.15 | 1.05 | 0.47 | 0.22 | 0.95 |
| Propionic acid | 0.70 | 0.26 | 1.18 | 0.71 | 0.35 | 0.16 | 0.56 |
| Allyl alcohol | 0.05 | 0.00 | 0.06 | 0.01 | 0.02 | 0.02 | 0.02 |
| Allyl acrylate | 0.06 | 0.00 | 0.11 | 0.00 | 0.02 | 0.01 | 0.00 |
| Propanaldehyde | 0.00 | 0.00 | 0.00 | 0.00 | 0.00 | 0.00 | 0.00 |
| Acetaldehyde | 0.13 | 0.06 | 0.15 | 0.06 | 0.04 | 0.03 | 0.00 |
| CO | 8.9 | 13.5 | 7.8 | 9.5 | 13.6 | 21.0 | 12.9 |
| $CO_2$ | 6.0 | 10.1 | 4.2 | 6.1 | 10.6 | 17.9 | 8.5 |
| Propylene | 14.4 | 11.4 | 16.3 | 13.9 | 7.0 | 4.7 | 7.4 |
| Quantity of oxygen consumed (*) (g O/kg catalyst) | 0.40 | 0.57 | 0.28 | 0.40 | 0.39 | 0.61 | 0.33 |
| Flow: Quantity of oxygen consumed per second (g O/kg catalyst/s) | 0.0301 | 0.0427 | 0.0211 | 0.0299 | 0.0295 | 0.0456 | 0.0243 |
| Conversion ratio propane (kg catalyst (1 bed)/kg converted propane) | 3476 | 2623 | 4268 | 3464 | 2107 | 1613 | 2456 |
| Yields (%) | | | | | | | |
| Acrylic acid | 12.3 | 15.3 | 9.0 | 12.6 | 21.0 | 23.7 | 17.8 |
| Acetic acid | 2.24 | 1.83 | 1.68 | 1.71 | 3.36 | 3.13 | 3.47 |
| Acrolein | 0.04 | 0.02 | 0.03 | 0.02 | 0.02 | 0.04 | 0.00 |
| Acetone | 0.22 | 0.13 | 0.34 | 0.22 | 0.17 | 0.11 | 0.29 |
| Propionic acid | 0.15 | 0.07 | 0.19 | 0.15 | 0.13 | 0.08 | 0.17 |
| Allyl alcohol | 0.01 | 0.00 | 0.01 | 0.00 | 0.01 | 0.01 | 0.01 |
| Allyl acrylate | 0.01 | 0.00 | 0.02 | 0.00 | 0.01 | 0.00 | 0.00 |
| Propanaldehyde | 0.00 | 0.00 | 0.00 | 0.00 | 0.00 | 0.00 | 0.00 |
| Acetaldehyde | 0.03 | 0.02 | 0.02 | 0.01 | 0.01 | 0.01 | 0.00 |
| CO | 1.88 | 3.60 | 1.22 | 1.97 | 4.89 | 10.11 | 3.93 |
| $CO_1$ | 1.26 | 2.72 | 0.66 | 1.27 | 3.79 | 8.58 | 2.59 |
| Propylene | 3.04 | 3.07 | 2.55 | 2.88 | 2.51 | 2.27 | 2.27 |
| Propane | 77.0 | 69.5 | 81.3 | 76.9 | 62.0 | 50.4 | 67.4 |
| Carbon balance(%) | 98.1 | 96.3 | 96.9 | 97.7 | 97.9 | 98.4 | 98.0 |

(*): in the double RISER test, the oxygen consumption was calculated on the total mass of catalyst (sum of the two beds).

It is seen that on 1 or 2 beds, the same quantity of oxygen is extracted from the catalyst (in g/kg catalyst), and with the same flow rate (same flow values g/kg.s). By contrast, the conversion ratio is calculated by considering only one bed, because it reflects the flow rate of solid necessary to convert 1 kg of propane. Since the unit operates at a maximum density (limited by the flow of catalyst), the only way to method they are less than 15.5%. Thus, the use of the two reactors allows a gain in conversion per pass to be obtained, without loss of selectivity. This allows the conversion ratio to be reduced, recalculated per reactor, but taking account of the total conversion, because the use of a second reactor involves increasing the flow of catalyst, in a unit which is often already at the maximum of solid density.

The invention claimed is:

1. A process for manufacturing acrylic acid from propane, wherein:
   a) a gaseous mixture devoid of molecular oxygen and comprising propane, water vapor, as well as, if appropriate, an inert gas, is introduced into a first reactor with a moving catalyst bed,
   b) at the outlet of the first reactor, the gases are separated from the catalyst;
   c) the catalyst is returned into a regenerator;
   d) the gases are introduced into a second reactor with a moving catalyst bed;
   e) at the outlet of the second reactor, the gases are separated from the catalyst and the acrylic acid contained in the separated gases is recovered;
   f) the catalyst is returned into the regenerator;
   g) the regenerated catalyst from the regenerator is reintroduced into the first and second reactors;

and wherein the catalyst comprises molybdenum, vanadium, tellurium or antimony, oxygen and at least one other element X chosen from niobium, tantalum, tungsten, titanium, aluminum, zirconium, chromium, manganese, iron, ruthenium, cobalt, rhodium, nickel, palladium, platinum, antimony, bismuth, boron, indium and cerium.

2. A process according to claim 1, wherein the first and second reactors are vertical and the catalyst is moved upwards by the gas flow.

3. A process according to claim 1, wherein the temperature of the reactors is comprised between 200 to 5000° C.

4. A process according to claim 1, wherein the temperature of the reactors is comprised between 250 to 4500° C.

5. A process according to claim 1, wherein the pressure in the reactors is comprised between $1.01 \times 10^4$ and $1.01 \times 10^6$ Pa (0.1 to 10 atmospheres).

6. A process according to claim 1, wherein the pressure in the reactors is comprised between $5.05 \times 10^4$ and $5.05 \times 10^5$ Pa (0.5-5 atmospheres).

7. A process according to claim 1, wherein the residence time of the gases in each reactor is comprised between 0.01 and 90 seconds.

8. A process according to claim 1, wherein the residence time of the gases in each reactor is comprised between 0.1 and 30 seconds.

9. A process according to claim 1, wherein the regeneration of the catalyst is carried out by heating in the presence of oxygen or a gas containing oxygen, at a temperature of 250 to 5000° C.

10. A process according to claim 1, wherein the propylene produced originating from the gases separated in stage e) or the propane which has not reacted or both are recycled to the inlet of the reactor.

11. A process according to claim 1, wherein the proportions of the elements of the catalyst meet the following conditions:

$$0.25 < r_{Mo} < 0.98$$

$$0.003 < r_V < 0.5$$

$$0.003 < r_{Te} \text{ or } r_{Sb} < 0.5$$

$$0.003 < r_x < 0.5$$

wherein $r_{Mo}$, $r_V$, $r_{Te}$ and $r_x$ represent the mole fractions, respectively, of Mo, V, Te and X, in relation to the sum of the numbers of moles of all the elements of the catalyst, with the exception of oxygen.

12. A process according to claim 1, wherein the catalyst corresponds to formula (I) or to formula (Ia) below:

$$Mo_1V_aTe_bNb_cSi_dO_x \qquad (I)$$

$$Mo_1V_aSb_bNb_cSi_dO_x \qquad (Ia)$$

wherein:
   a) a is comprised between 0.006 and 1, inclusive;
   b) b is comprised between 0.006 and 1, inclusive;
   c) c is comprised between 0.006 and 1, inclusive;
   d) d is comprised between 0 and 3.5, inclusive; and
   e) x is the quantity of oxygen bound to the other elements and depends on their oxidation states.

13. A process according to claim 12, wherein, in formula (I) or (Ia):
   a is comprised between 0.09 and 0.8, inclusive;
   b is comprised between 0.04 and 0.6, inclusive;
   c is comprised between 0.01 and 0.4, inclusive; and
   d is comprised between 0.4 and 1.6, inclusive.

14. A process according to claim 1, wherein, at least one of the two reactors comprises a cocatalyst corresponding to the following formula (II):

$$Mo_1Bi_{a'}Fe_{b'}Co_{c'}Ni_{d'}K_{e'}Sb_{f'}Ti_{g'}Si_{h'}Ca_{i'}Nb_{j'}Te_{k'}Pb_{l'}W_{m'}Cu_{n'} \qquad (II)$$

wherein:
   a' is comprised between 0.006 and 1, inclusive
   b' is comprised between 0 and 3.5, inclusive;
   c' is comprised between 0 and 3.5, inclusive;
   d' is comprised between 0 and 3.5, inclusive;
   e' is comprised between 0 and 1, inclusive;
   f' is comprised between 0 and 1, inclusive;
   g' is comprised between 0 and 1, inclusive;
   h' is comprised between 0 and 3.5, inclusive;
   i' is comprised between 0 and 1, inclusive;
   j' is comprised between 0 and 1, inclusive;
   k' is comprised between 0 and 1, inclusive;
   l' is comprised between 0 and 1, inclusive;
   m' is comprised between 0 and 1, inclusive; and
   n' is comprised between 0 and 1, inclusive.

15. A process according to claim 14 wherein the cocatalyst is regenerated and circulates in the same way as the catalyst.

16. A process according to claim 14, wherein, in the cocatalyst of formula(II):
   a' is comprised between 0.01 and 0.4, inclusive;
   b' is comprised between 0.2 and 1.6, inclusive;
   c' is comprised between 0.3 and 1.6, inclusive;
   d' is comprised between 0.1 and 0.6, inclusive;
   e' is comprised between 0.006 and 0.01, inclusive;
   f' is comprised between 0 and 0.4, inclusive;
   g' is comprised between 0 and 0.4, inclusive;
   h' is comprised between 0.01 and 1.6, inclusive
   i' is comprised between 0 and 0.4, inclusive;
   j' is comprised between 0 and 0.4, inclusive;
   k' is comprised between 0 and 0.4, inclusive;
   l' is comprised between 0 and 0.4, inclusive;
   m' is comprised between 0 and 0.4, inclusive; and
   n' is comprised between 0 and 0.4, inclusive.

17. A process according to claim 14, wherein, a weight ratio of the catalyst to the cocatalyst greater than 0.5 is used.

18. A process according to claim 14, wherein, a weight ratio of the catalyst to the cocatalyst of at least 1 is used.

19. A process according to claim 14, wherein the catalyst and the cocatalyst are mixed.

20. A process according to claim 14, wherein the catalyst and the cocatalyst are present in the form of pellets, each pellet comprising both the catalyst and the cocatalyst.

21. A process for manufacturing acrylic acid from propane, wherein:
  a) a gaseous mixture devoid of molecular oxygen and comprising propane, water vapor, as well as, if appropriate, an inert gas, is introduced into a first reactor with a moving catalyst bed,
  b) at the outlet of the first reactor, the gases are separated from the catalyst;
  c) the catalyst is returned into a regenerator;
  d) the gases are introduced into a second reactor with a moving catalyst bed;
  e) at the outlet of the second reactor, the gases are separated from the catalyst and the acrylic acid contained in the separated gases is recovered;
  f) the catalyst is returned into the regenerator;
  g) the regenerate catalyst from the regenerator is reintroduced into the first and second reactors;

wherein:
  the first and second reactors are verticle and the catalyst is moved upwards by the gas flow;
  the temperature of the reactors is comprised between 250 to 450° C.;
  the pressure in the reactors is comprised between $5.05 \times 10^4$ and $5.05 \times 10^5$ Pa (0.5-5 atmospheres);
  the residence time of the gases in each reactor is comprised between 0.1 and 30 seconds;
  the catalyst corresponds to formula (I) or to formula (Ia) below:

$$Mo_1V_aTe_bNb_cSi_dO_x \quad (I)$$

$$Mo_1V_aSb_bNb_cSi_dO_x \quad (Ia)$$

wherein:
  h) a is comprised between 0.006 and 1, inclusive
  i) b is comprised between 0.006 and 1, inclusive
  j) c is comprised between 0.006 and 1, inclusive
  k) d is comprised between 0 and 3.5, inclusive; and
  l) x is the quantity of oxygen bound to the other elements and depends on their oxidation states.

22. A process for manufacturing according to claim 17 wherein, in formula (I) or (Ia):
  a is comprised between 0.09 and 0.08, inclusive
  b is comprised between 0.04 and 0.6, inclusive
  c is comprised between 0.01 and 0.4, inclusive
  d is comprised between 0.4 and 1.6, inclusive.

23. A process according to claim 17, wherein, the propylene produced originating from the gases separated in stage e) or the propane which has not reacted or both are recycled to the inlet of the reactor.

24. A process according to claim 17 wherein, at least one of the two reactors comrises a cocatalyst corresponding to the following formula (II):

$$Mo_1Bi_{a'}Fe_{b'}Co_{c'}Ni_{d'}K_{e'}Sb_{f'}Ti_{g'}Si_{h'}Ca_{i'}Nb_{j'}Te_{k'}Pb_{l'}W_{m'}Cu_{n'} \quad (II)$$

wherein:
  a' is comprised between 0.006 and 1, inclusive
  b' is comprised between 0 and 3.5, inclusive
  c' is comprised between 0 and 3.5, inclusive;
  d' is comprised between 0 and 3.5, inclusive;
  e' is comprised between 0 and 1, inclusive;
  f' is comprised between 0 and 1, inclusive;
  g' is comprised between 0 and 1, inclusive;
  h' is comprised between 0 and 3.5, inclusive;
  i' is comprised between 0 and 1, inclusive;
  j' is comprised between 0 and 1, inclusive;
  k' is comprised between 0 and 1, inclusive;
  l' is comprised between 0 and 1, inclusive;
  m' is comprised between 0 and 1, inclusive; and
  n' is comprised between 0 and 1, inclusive.

* * * * *